United States Patent [19]

Davidson et al.

[11] 4,400,383

[45] Aug. 23, 1983

[54] TREATMENT OF ANXIETY

[75] Inventors: Jonathan R. T. Davidson, Chapel Hill; Anthony T. Dren, Raleigh, both of N.C.

[73] Assignee: Burroughs Wellcome Co., Research Triangle Park, N.C.

[21] Appl. No.: 413,078

[22] Filed: Aug. 30, 1982

Related U.S. Application Data

[63] Continuation-in-part of Ser. No. 329,880, Dec. 11, 1981, abandoned.

[51] Int. Cl.³ .................................... A61K 31/495
[52] U.S. Cl. ............................................ 424/250
[58] Field of Search .................................. 424/250

[56] References Cited

FOREIGN PATENT DOCUMENTS

78/7352 of 0000 South Africa .

OTHER PUBLICATIONS

Drugs, vol. 22, No. 6, pp. 495–514, Dec. 1981.

*Primary Examiner*—Stanley J. Friedman
*Attorney, Agent, or Firm*—Donald Brown

[57] ABSTRACT

This invention is directed to the use of a carbazole compound 9-[3-(3,5-cis-dimethylpiperazino)propyl]carbazole, its salts, especially pharmaceutically acceptable salts, and solvates such as hydrates, alcoholates of the salts thereof as well as pharmaceutical compositions containing same in treating anxiety such as generalized anxiety disorder, etc., in humans.

26 Claims, No Drawings

TREATMENT OF ANXIETY

Prior Application

This application is a continuation-in-part of U.S. patent application Ser. No. 329,880 filed Dec. 11, 1981, now abandoned.

FIELD OF THE INVENTION

The present invention relates to compounds and pharmaceutical compositions containing them, for use in human medicine in the treatment of anxiety and in particular Generalized Anxiety disorder in a patient previously identified as having or having had Generalized Anxiety disorder symptoms or other symptoms associated with other anxiety disorders e.g., Phobia and Panic disorders.

PRIOR ART

Australian Pat. No. 201630 and French Pat. No. 1167510 describe as having anti-epileptic properties carbazoles of formula (I):

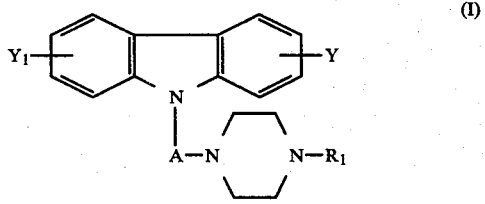

(I)

wherein A represents a divalent saturated aliphatic hydrocarbon radical with a straight or branched chain containing 2 to 6 carbon atoms, $R_1$ represents a hydrogen atom or a lower alkyl or an aryl or araliphatic group, Y and $Y_1$ are respectively a hydrogen or halogen atom or a lower alkyl, alkoxy, aryl or aryloxy group, the ring containing Y or $Y_1$ may contain substituents additional to Y and $Y_1$ and one or more of the carbon atoms of the piperazine ring may carry a substituent in the form of a methyl group.

South African Pat. No. 78/7352 discloses the compound disclosed herein for use in treating agression and psychosis.

DESCRIPTION OF THE INVENTION

The compound 9-[3-(3,5-cis-dimethylpiperazino)-propyl]carbazole (sometimes named as cis-9-[3-(3,5-dimethylpiperazinyl)-propyl]carbazole or 9-[3-(cis-3,5-dimethyl-1-piperazinyl)-propyl]carbazole) of formula (A):

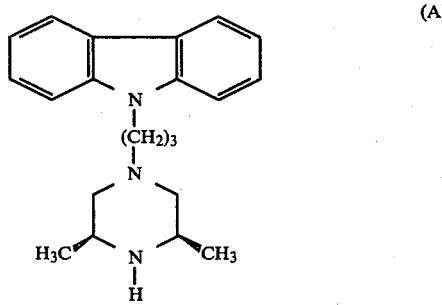

(A)

hereinafter referred to as the "Carbazole," its pharmaceutically acceptable salts and pharmaceutically acceptable solvates of its pharmaceutically acceptable salts previously had been found to unexpectedly exhibit valuable anti-aggressive and anti-psychotic properties rendering them useful for the treatment of aggression and psychoses in humans. The compounds herein unexpectedly do not exhibit the toxic side-effects, e.g. extrapyramidal dysfunction or sedative action associated with anti-psychotics such as chlorpromazine and the like. These compounds have now unexpectedly also been found useful for the treatment of humans suffering from anxiety e.g., anxiety associated with certain schizophrenic patients. The compounds of this invention are also useful in treating patients having been identified as having or having had general anxiety disorder, Phobic disorder (Phobic Neuroses), Panic disorder, Obsessive Compulsive disorder and Post-Traumatic Stress disorder.

As used herein, the term "treatment" is meant to include the prophylactic administration of the "Carbazole" to a patient (human) who has already been identified as once having exhibited anxiety symptoms as well as the therapeutic administration of the "Carbazole" to a patient (human) exhibiting anxiety symptoms.

The clinical procedure used to evaluate the anti-anxiety effects is based on the *Brief Psychiatric Rating Scale* described by J. E. Overall and D. R. Gorham, Psychol. Rep., 10, 799–812 (1962) and the Inpatient Multidimensional Psychiatric Scale described by M. Lorr et al., in the manual on this test, Consulting Psychologists Press, Palo Alto, Calif., (1963).

The "Carbazole" is particularly valuable since its anti-anxiety action is substantially free from undesirable side-effects such as sedation, catalepsy and extrapyramidal dysfunction. An indication that the "Carbazole" does not interfere with extrapyramidal function is its failure to antagonise apomorphine-induced stereotyped behaviour in the rat (see Andien, N. E., *J. Psychiat. Res.*, 11, 97, 1974. There is also significantly less anti-cholinergic and anti-histamine activity associated with the "Carbazole's" action than with the phenothiazines.

Whilst the useful biological properties of the "Carbazole" reside in the basic moiety, it is capable of forming acid addition salts, and all such salts are included within the scope of the invention. Non-pharmaceutically acceptable salts may be used as intermediates for conversion to corresponding pharmaceutically acceptable salts. Examples of pharmaceutically acceptable salts are the halides, especially mono- and di-hydrochloride, sulphate and anions of organic acids such as tosylate, methanesulphonate, tartrate and maleate. In addition, the base moiety of the "Carbazole" can form well-defined solvates of the salts e.g. hydrates, as well as solvates of alcohols e.g. ethanol, methanol and these solvates are also included within the scope of the invention.

The "Carbazole" may be synthesised by any method known in the art for the synthesis of compounds having an analogous structure.

1. A preferred synthesis involves linking the alkylene chain to either or both of the carbazole and piperazine rings. This may be done by reacting a compound of formula (II), (IIA) or (IIB) as appropriate, wherein each Z is a leaving atom or group;

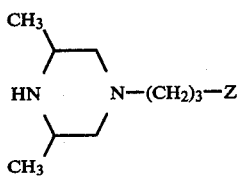

(II)

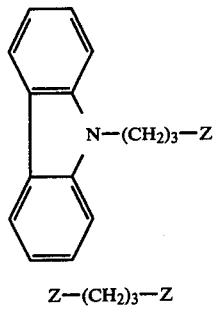

(IIA)

Z—(CH₂)₃—Z (IIB)

with carbazole, 3,5-dimethylpiperazine or both carbazole and 3,5-dimethylpiperazine, respectively. Any atom or group may be used for the variable Z which enables substitution to take place on the appropriate amino group; for example, halo (preferably chloro), arylsulphonyloxy (preferably p-toluenesulphonyloxy) or alkylsulphonyloxy (preferably methanesulphonyloxy).

Although compounds (II) and (IIB) will react directly with carbazole it is advantageous to use a carbazole derivative; particularly suitable derivatives are those with alkali or alkaline earth metals, especially lithium, sodium, potassium, zinc, cadmium and calcium, although carbazole magnesium halide, e.g., iodide, may also be used.

The alkali metal carbazoles are conveniently prepared by reacting carbazole with the appropriate alkali metal hydride or amide in an inert, preferably polar, aprotic solvent such as liquid ammonia, dimethylformamide or dimethylsulphoxide; other solvents which may be suitable include hydrocarbons, e.g., alkanes, cycloalkanes and aromatic compounds. The same reaction medium may then be used for effecting N-substitution which is preferably carried out with heating. It is advisable that the N-substitution take place in solution under an inert atmosphere such as nitrogen.

Alternatively, the compound of formula (II) may be reacted with carbazole in the presence of an alkali metal hydroxide or alkali metal alkoxide in a polar solvent such as dimethylformamide, dimethylacetamide, water or the corresponding alkanol as appropriate; for example potassium tert-butoxide in tert-butanol.

When 3,5-dimethylpiperazine is reacted with a compound of formula (IIA) this may be done in a polar aprotic solvent such as dimethylformamide, dimethylsulphoxide, or acetonitrile or a protic solvent such as water or an aliphatic alcohol.

The intermediates of formula (II) are readily obtained from the corresponding alcohol by conventional techniques. For example, the alcohol may be converted to the chloride by reaction with thionyl chloride. The alcohol may itself be made by reaction of a substituted alcohol of formula Z—(CH₂)₃—OH, wherein Z has the same meaning as in formula (II), with 3,5-dimethylpiperazine.

Synthesis of intermediates of formula (IIA) may be by N-substitution analogous to the reaction of compound (IIB) with carbazole to produce a compound of formula (I).

A modification of the previously described synthesis is to use intermediates of formula (II) or (IIA) which, instead of using a leaving group Z, have a double bond between the terminal and penultimate carbon atoms; thus effecting an addition, rather than a substitution, reaction. The reaction may be effected at high temperatures and pressures in the presence of an alkali, such as in an autoclave at a temperature up to 120° for example about 115° C. with an alkali metal hydroxide such as sodium hydroxide. Desirably an equimolar amount of alkali is used.

Similarly intermediates of formula (II) and (IIA) may themselves be obtained by an addition reaction involving a Michael-type condensation of a piperazine or carbazole, respectively with acrylic acid or a derivative thereof such as acid halide, ester, amide or nitrile. The resulting compound may then be reduced to the corresponding alcohol.

2. The "Carbazole" may also be synthesized by reduction of a compound of formula (III):

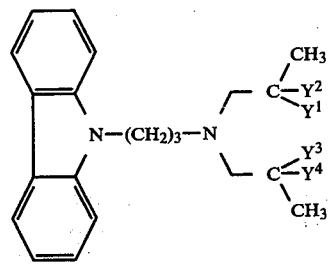

(III)

wherein $Y^1$ and $Y^2$ together form oxo, thioxo or imino, or $Y^1$ is hydroxy and $Y^2$ is hydrogen, and the groups $Y^3$ and $Y^4$ are defined in the same way as $Y^1$ and $Y^2$, with the proviso that both $Y^1$ and $Y^3$ may not be hydroxy, except that when $Y^1$ to $Y^4$ do not include a nitrogen atom the reduction takes places in the presence of ammonia or an ammonium salt such as ammonium chloride.

Many reducing agents are suitable for this purpose depending on the particular case concerned. For example, hydrogen in the presence of (Raney) nickel or palladium, or zinc in the presence of an acid. Or, after an initial cyclisation of the compound of formula (III), lithium aluminium hydride, Vitride ®, diborane and other aluminium and boron hydrides known to reduce amides may be used.

When, in formula (III), one of $Y^1$ and $Y^2$ and one of $Y^3$ and $Y^4$ is hydroxy the compound is readily cyclised in the presence of ammonia to the "Carbazole" without the aid of a reducing agent. Reaction conditions may be selected from those known in the art as suitable for ammonolysis reactions, for example, heating under pressure in the presence of a catalyst such as copper chromite or alumina, optionally in the presence of an inert solvent.

The intermediates of formula (III) may be prepared by reaction of a compound of formula (V) with 3-(9-carbazolyl)propylamine of formula (IV):

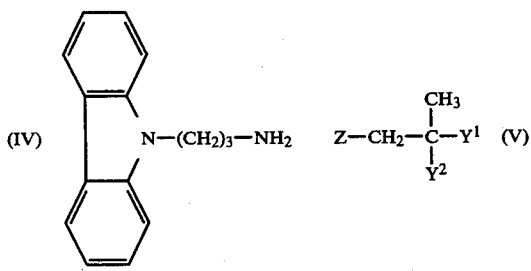  

wherein Z, $Y^1$ and $Y^2$ are as defined above in formulae (II) and (III) respectively; in a molar ratio of 2 to 1. The reaction is conveniently carried out in an inert polar solvent at an elevated temperature, and in the presence of an acid acceptor such as tri-ethylamine to sequester hydrogen ions which are liberated in the reaction.

Intermediates of formula (III) suitable for conversion to compounds of formula (I) by ammonolysis may themselves be prepared by reacting the amine (IV) with 1,2-epoxypropane of formula (VI):

$$CH_3-CH-\underset{O}{\overset{}{\diagup\!\!\!\diagdown}}-CH_2 \qquad (VI)$$

The reaction will proceed if the reactants are simply heated together at about 100° C., but optionally a lower alkanol is used as a solvent in which case a lower temperature such as from 45° to 60° C. may be used. By lower alkanol is meant an alkanol having 1 to 6 carbon atoms for example, methanol, ethanol, butanol or hexanol.

The compound of formula (IV) may be obtained by ammonolysis of the corresponding alcohol or halide, preferably using a large excess of ammonia under pressure often in the presence of a catalyst such as copper chromite or alumina, or reduction of the appropriate nitrile or amide. The desired alcohol, halide, nitrile or amide may be prepared by methods described above for the preparation of compounds of formula (IIA).

3. A number of syntheses of the "Carbazole" involve, as the last step, the reduction of an analogous carbonyl compound of formula (VII):

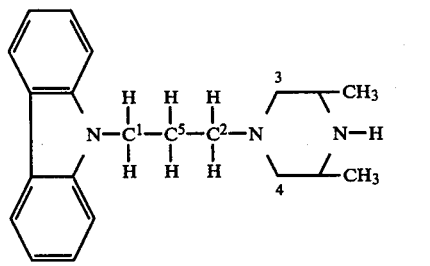

(a) wherein the two hydrogens on one or more of the carbons numbered 1 to 4 are replaced by an oxo group (Most reagents capable of reducing an amide carbonyl group may be used for example hydrogenation at elevated temperature and pressure using nickel, platinum, palladium or copper chromite as a catalyst; concentrated hydriodic acid with red phosphorous; and particularly suitable are lithium aluminium hydride or diborane. Electrolytic reduction may also be used.); or (b) wherein the two hydrogens on the carbon numbered 5 are replaced by an oxo group. [Most reagents capable of reducing a ketone group may be used, for example hydrogenation using nickel, platinum, palladium or copper chromite as a catalyst at elevated temperature and pressure; zinc and hydrochloric acid (Clemmensen); hydrazine in the presence of a base (Wolff-Kishner)].

The compounds of formula (VII) wherein the oxo group is on either of carbons numbered 3 or 4 may be made by a reaction analogous to that described above involving a compound of formula (IIA), but using a substituted piperazine of formula (VIII):

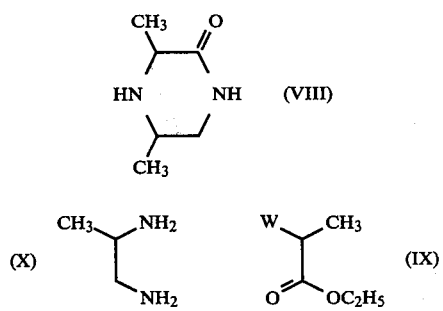

A convenient preparation of (VIII) is by reaction of a compound of formula (IX) with a large excess of 1,2-diaminopropane of formula (X):

wherein W is a leaving group such as halo e.g. chloro or bromo, or alkylthio. The reaction may be carried out by simply heating the reactants although it is preferable to use an inert solvent such as acetonitrile or dioxane, and it is particularly advantageously to use a lower alkanol such as ethanol as a solvent.

Alternatively, compounds of formula (VII) may be prepared by reacting a piperazine or carbazole, or a reactive derivative thereof such as are described hereinabove, with an acrylyl halide such as acrylyl chloride or alkyl acrylate to provide a compound of formula $C/P.CO.CH:CH_2$ wherein C/P is 3,5-dimethylpiperazinyl or carbazolyl, respectively, followed by reaction with carbazole or 3,5-dimethylpiperazine as appropriate.

The compound of formula (VII) wherein the oxo group is on the carbon numbered 5 may be prepared, for example, by the reaction of $\alpha,\alpha'$-dichloroacetone with 2,5-dimethylpiperazine in ethanol to give 4-(3-chloro-2-oxopropyl)-2,5-dimethylpiperazine which in turn is caused to react with carbazole in dimethylformamide in the presence of a strong base such as sodium hydride.

4. The "Carbazole" may also be made by formation of the carbazole nucleus as the final step, for example, from the corresponding phenothiazine analogues by heating with copper.

Alternatively, the diphenylamine of formula (XI):

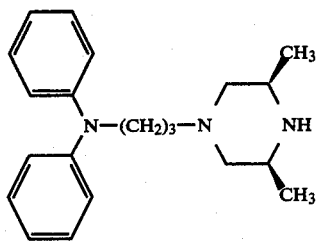

(XI)

may be ring-closed by the reaction of a palladium (II) salt in a polar solvent. The preferred palladium (II) salts are the acetate and chloride which are generally used in equimolar amount with the diphenylamine. Preferred solvents are acetic acid, acetonitrile, sulpholane and especially trifluoroacetic acid, and the reaction is advantageously effected at an elevated temperature up to the reflux temperature of the reaction medium.

The reaction is conveniently carried out in the presence of catalytic amounts of a strong acid or boron trifluoride.

A further synthesis of the "Carbazole" is by oxidation of the corresponding 1,2,3,4-tetrahydro derivative (or the analogous octahydro compound). Any conventional dehydrogenating agent may be used provided that it does not oxidize any of the nitrogens in the remainder of the molecule, for example $Pb_3O_4$, chromic oxide, alumina, a quinone such as tetrachloroquinone, or catalytically over hot platinum or palladium.

Synthesis of the intermediate phenothiazines, diphenylamines and tetrahydrocarbazoles may be done using conventional techniques well-known in the art.

5. Completion of the substituted piperazine ring may also be used to synthesize the "Carbazole."

The compound of formula (XII) may be reacted with a compound of formula (XIII):

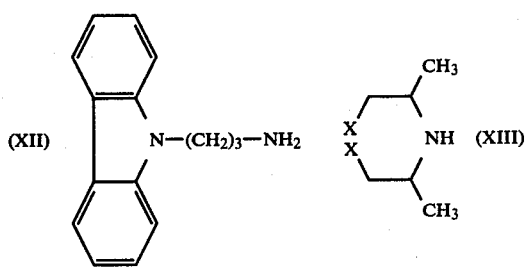

wherein X is a leaving group such as halide, preferably iodo or bromo, hydroxy, sulphate or a sulphonate easter such as a p-toluenesulphonate. The reaction may be carried out with heating in a polar solvent such as acetone or a lower alkanol by which is meant alkanols having 1 to 6 carbon atoms such as ethanol or butanol.

The "Carbazole," its pharmaceutically acceptable salts and solvates of these salts are useful in the treatment of anxiety disorders in humans diagnosed as suffering from these disorders according to the criteria set forth in the *Diagnostic and Statistical Manual of Mental Illness* (DSM-III), published by the American Psychiatric Association, Washington, D.C., (1980). As used herein "anxiety" is defined as including apprehension, fatigue or agitation arising from situational disturbances or organic disorder.

The "Carbazole" compound, its pharmaceutically acceptable salts and solvates of these pharmaceutically acceptable salts are administered to mammals, e.g., humans, preferably orally at a dose of 0.25 mg to 15 mg/kg per day (calculated as base) of bodyweight of the mammal being treated for anxiety disorders e.g., those mentioned above namely generalized anxiety disorder, panic disorders, obsessional compulsive disorder, phobic disorders and post traumatic stress disorders and most preferably 1 to 10 mg/kg is preferably administered orally at this dose to treat these disorders. The "Carbazole" compound, its pharmaceutically acceptable salts and solvates are preferably given one to four times daily at the aforementioned dose for these conditions. For intramuscular injection the dose is generally one-half the oral dose. For example, for anxiety a suitable dose would be in the range of 0.25 mg/kg to 15 mg/kg and most preferably 1 mg/kg to 10 mg/kg, for example as a unit oral dose of from 25 to 400 mg most preferably a unit oral dose 25 to 100 mg. Conveniently the unit dose is administered one or more times daily, for example as one or more tablets each containing from 10 to 300, conveniently 25 mg or 50 mg of the "Carbazole," its pharmaceutically salts or its solvates taken four times a day may be used in treating generalized anxiety disorder, panic disorders, phobic disorders, obsessional compulsive disorder and post traumatic stress disorders.

Generally, to treat the afformentioned disorders the carbazole and salt, solvate thereof will be administered for period of 1 week to 1 month. Although for use in medicine, the "Carbazole" or a salt thereof may be administered as a raw chemical, it is preferably presented with an acceptable carrier therefor as a pharmaceutical composition. The carrier must be course be 'acceptable' in the sense of being compatible with the other ingredients of the composition and not deleterious to the recipient of the composition. The carrier may be a solid or a liquid or a mixture of solid and liquid substance, and is preferably formulated with the Carbazole or a salt thereof as a unit-dose composition, for example, a tablet, capsule or cachet for oral administration or a suppository for rectal administration. Other pharmaceutically active substances may also be present in compositions of the present invention, and the compositions may be formulated by any of the well-known techniques of pharmacy consisting basically of admixture of the components. For example, tablets may be made by granulating, grinding, stirring, coating, milling, tumbling, compressing or molding.

Unit dose compositions, for rectal or parenteral administration conveniently contain from 5 mg to 75 mg of the "Carbazole" base or a pharmaceutically acceptable salt or solvate thereof calculated as base.

For the oral administration, fine powders or granules of the compounds may contain diluents and dispersing and surface active agents, and may be presented in a draught in water or in a syrup, in capsules or cachets in the dry state or in an aqueous or non-aqueous suspension, when a suspending agent may also be included; in tablets, preferably made from granules of the active ingredient with a diluent, by compression with binders and lubricants; or in a suspension in water or a syrup or an oil or in a water/oil emulsion, when flavoring, preserving, suspending, thickening and emulsifying agents may also be included. The granules or the tablets may be coated, and the tablets may be scored.

For parenteral administration (by intramuscular, intravenous, intraperitoneal or subcutaneous injection), the "Carbazole" preferably as a pharmaceutically acceptable salt or hydrate may be presented in unit dose or multi-dose containers in aqueous or non-aqueous injection solutions which may contain antioxidants, buffers, bacteriostats and solutes which render the compounds isotonic with the blood; or in aqueous or non-aqueous suspensions when suspending agents and thickening agents may also be included; extemporaneous injection solutions and suspensions may be made from sterile powders, granules or tablets which may contain diluents, dispersing and surface active agents, binders and lubricants.

It will be understood from the foregoing description that what we will claim in accordance with this invention may comprise any novel feature described herein, principally but not exclusively as follows:

A method for the treatment or prophylaxis of a mammal (e.g., human) which is subject to an anxiety condition which is susceptable to treatment e.g., of the type mentioned above comprising adminstration to said mammal of a nontoxic, effective anti-anxiety amount to the "Carbazole" or a pharmaceutically acceptable salt or solvate thereof as hereinbefore defined. The diagnosis of the various anxiety disorders, such as Generalized Anxiety Disorder, is based on the Manual entitled Diagnostic and Statistical Manual of Mental Illness (DSM - III), p 225 to 239, a publication of the American Physciatric Association.

In the group of disorders treated herein anxiety is either the predominant disturbance as in Panic Disorder and Generalized Anxiety Disorder, or anxiety is experienced if the individual attempts to master the symptoms, as in confronting the dreaded object or situation in a Phobic Disorder or resisting the obsessions or compulsions in Obsessive Compulsive Disorder. Diagnosis of an Anxiety Disorder is not made if the anxiety is ude to another disorder, such as Schizophrenia, an Affective Disorder, or an Organic Mental Disorder.

The following Examples are given by way of illustration of the invention: they are not to be construed as a limitation thereof. In these Examples all temperature are in degrees Celsius and vacuum distillation was effected on a steam bath using a pressure of about 20 mm Hg, unless otherwise specified.

EXAMPLE 1

Preparation of 9-[3-(3,5-cis-dimethylpiperazino)-propyl]carbazole dihydrochloride hemihydrate.

A. 3-(3,5-cis-Dimethylpiperazino)propanol dihydrochloride 2,6-cis-Dimethylpiperazine (114.2 g, 1.0 mole), 3-chloropropanol (94.5 g, 1.0 mole), sodium carbonate (105 g) and ethylene glycol monomethyl ether (400 ml) were stirred under reflux for four hours. The reaction mixture was filtered warm, and the filtrate stripped of solvent by vacuum distillation.

The resulting solid was dissolved in ethanol (500 ml), and this solution saturated with dry hydrogen chloride. The white precipitate was collected, dried in vacuo, and used as the hydrochloride salt in the next step without further purification, m.p. 240°-241°.

B. 3-(3,5-cis-Dimethylpiperazino)propyl chloride dihydrochloride

Thionyl chloride (300 g) was slowly added to 3-(3,5-cis-dimethylpiperazino)propanol dihydrochloride (200 g). The reaction was gently refluxed for an hour followed by removal of excess thionyl chloride by vacuum distillation. The resulting solid was washed with several portions of benzene then several portions of ether, m.p. 291°-292°.

C. 9-[3-(3,5-cis-Dimethylpiperazino)propyl]-carbazole dihydrochloride hemihydrate To a slurry of sodium hydride (1.6 mole) made from 70 g of 57% dispersion in mineral oil and 200 ml of dimethylformamide (DMF) was added a solution of carbazole (83.5 g, 0.5 mole) in DMF (150 ml). When hydrogen was no longer evolved a slurry of 3-(3,5-cis-dimethylpiperazino)propyl chloride dihydrochloride (131 g, 0.5 mole) in DMF (200 ml) was added to the reaction at a slow rate. The reaction was run under nitrogen using a demand system with an oil bubbler. There was some foaming as the slurry was added and the rate of addition was adjusted to keep this to a minimum. After addition was completed the reaction was heated (90°-120°) for 16 to 18 hours, cooled, filtered and stripped of solvent by vacuum distillation. The viscous residue was warmed with 2 liters of 1 N hydrochloric acid, cooled, and washed with ether (500 ml). The ether layer which contained any unreacted carbazole was discarded. The aqueous layer was treated with activated charcoal and filtered through Celite ®. The filtrate was made basic to Alkacid ® paper using sodium hydroxide, and then extracted with ether four times. Both ether and aqueous layers were clear at the end of the extraction. The ether layer was dried with anhydrous magnesium sulphate or molecular sieves and the hydrochloride salt of 9-[3-(3,5-dimethylpiperazino) propyl]carbazole was precipitated by passing dry hydrogen chloride into the solution. The precipitate was collected and recrystallized from ethyl acetate or ethanol/ether mixture giving 9-[3-(3,5-dimethylpiperazino)propyl]-carbazole dihydrochloride hemihydrate (50 g), m.p. 288°-290° C.

EXAMPLE 2

The compound of Example 1 was administered to male mice to ascertain the oral and intravenous $LD_{50}$'s which were found to be as follows:

| Oral | Intravenous |
|---|---|
| 977 mg/kg | 31 mg/kg |

EXAMPLE 3

Preparation of 9-[3,5-cis-dimethylpiperazino)-propyl]carbazole.

9-[3-(3,5-cis-Dimethylpiperazino)propyl]-carbazole dihydrochloride hemihydrate (150 g), anhydrous ethanol containing about 5% methanol (680 ml), water (275 ml) and 10 N sodium hydroxide (76 ml) were combined and heated to effect solution. Water (500 ml) was slowly added to the hot solution which was then allowed to cool slowly to room temperature. The mixture was further cooled to 0° for one hour and then filtered. The product was washed thoroughly with water and dried to give 9-[3-(3,5-cis-dimethylpiperazino)propyl]carbazole (110 g, 92% of theory), m.p. 107°-109°.

Calculated for $C_{21}H_{30}Cl_2N_3O_{0.5}$: C 78.46, H 8.47, N 13.07, Found: C 78.43, H 8.46, N 13.05.

EXAMPLE 4

9-[3-(3,5-cis-Dimethylpiperazino)propyl]-carbazole monohydrochloride

The 9-[3-(3,5-cis-dimethylpiperazino)propyl]-carbazole dihydrochloride hemihydrate (5 g) of Example 1 was dissolved in water (250 ml), and the solution was neutralized to pH 7 with 5 N sodium hydroxide. The resulting precipitate was collected by filtration, washed with water and dried under reduced pressure to give 9-[3-(3,5-cis-dimethylpiperazine)propyl]carbazole monohydrochloride (3.7 g), m.p. 309°–311° (dec.), which had the following elemental analysis:

Calculated for $C_{21}H_{28}N_3Cl$: C, 70.47; H, 7.89; N, 11.74; Cl, 9.91, Found: C, 70.53; H, 7.93; N, 11.69; Cl, 9.83.

EXAMPLE 5

9-[3-(3,5-cis-Dimethylpiperazino)propyl]-carbazole maleate

The 9-[3-(3,5-cis-dimethylpiperazino)propyl]-carbazole (10 g) of Example 4 was dissolved in warm acetone (71 ml). Maleic acid (3.7 g) was slowly added, causing precipitate formation. The resulting slurry was stirred while heating at reflux for 10 min. It was then cooled to room temperature and filtered. The collected precipitate was washed with acetone and then recrystallized from water to give 9-[3-(cis-dimethylpiperazino-propyl]carbazole maleate (10.5 g), m.p. 162°–163° (dec.), which had the following elemental analysis:

Calculated for $C_{25}H_{31}N_3O_4$: C, 68.63; H, 7.14; N, 9.60, Found: C, 68.91; H, 7.25; N, 9.74.

EXAMPLE 6

9-[3-(3,5-cis-Dimethylpiperazino)propyl]-carbazole lactate

The 9-[3-(3,5-cis-dimethylpiperazino)propyl]- carbazole (10 g) of Example 4 was dissolved in warm SD3A (ethanol containing about 5% methanol—50 ml) and succinic acid (3.8 g) was slowly added. The mixture was stirred and heated at reflux for 10 min. and then cooled to 5°. The product was collected by filtration and crystallized from SD3A/water (95/5 v/v) to give 9-[3-(3,5-cis-dimethylpiperazino)propyl]-carbazole three-fourths succinate (10.4 g), m.p. 175.5°–176.5° (stoichiometry confirmed by nmr), which had the following elemental analysis:

Calculated for $C_{24}H_{31.5}N_3O_3$: C, 70.30; H, 7.74; N, 10.24, Found: C, 70.21; H, 7.71; N, 10.20.

EXAMPLE 7 cis-9-[3,5-Dimethly-1-piperazinyl)propyl]-carbazole acetate one-quarter hydrate To the 9-[3-(3,5-cis-dimethylpiperazino)-propyl]-carbazole (10 g) of Example 4 dissolved in hot toluene (70 ml) was added acetic acid (2.0 ml). The mixture was stirred and cooled to 2°. The resulting product was collected by filtration, washed with cyclohexane (35 ml) and dried under reduced pressure to give cis-9-[3-(3,5-dimethyl-1-piperazinyl)propyl]carbazole acetate one-quarter hydrate (10.4 g), m.p. 144°–146°, which had the following elemental analysis:

Calculated for $C_{23}H_{31.5}N_3O_{2.25}$: C, 71.56; H, 8.22; N, 10.88, Found: C, 71.57; H, 8.08; N, 10.84.

EXAMPLE 8 cis-9-[3,5-Dimethyl-1-piperazinyl)propyl]-carbazole sulfate monohydrate

To the cis-9-[3-(3,5-dimethyl-1-piperazinyl)propyl]-carbazole (10 g) of Example 4 dissolved in warm acetone (100 ml) was slowly added with stirring a solution of sulfuric acid (3.05 g) in water (5 ml), causing immediate precipitation. The slurry was stirred at reflux for 10 min. and then cooled to 20°. The product was collected by filtration and washed with acetone (20 ml). It was reslurried in water (70 ml), filtered, washed with acetone (40 ml) and dried under reduced pressured to give cis-9-[3-(3,5-dimethyl-1-piperazinyl)propyl]carbazole sulfate monohydrate (12.9 g), m.p. 243°–246° (dec.), which had the following analysis:

Calculated for $C_{21}H_{31}N_3O_5S$: C, 57.46; H, 7.14; N, 9.60, Found: C, 57.75; H, 7.10; N, 9.47.

EXAMPLE 9

Following the procedure of Example 6, 9-[3-(3,5-cis-dimethylpiperazino)propyl]carbazole was allowed to react with an equimolar amount of the appropriate acid to give the following salts:

9-[3-(3,5-cis-dimethylpiperazino)propyl]carbazole fumarate

9-[3-(3,5-cis-dimethylpiperazino)propyl]carbazole citrate

9-[3-(3,5-cis-dimethylpiperazino)propyl]carbazole L-malate

9-[3-(3,5-cis-dimethylpiperazino)propyl]carbazole L-tartrate

9-[3-(3,5-cis-dimethylpiperazino)propyl]carbazole methanesulfonate.

Pharmaceutical Formulations

In the following examples of pharmaceutical formulations according to the present invention, unless otherwise indicated, the term "Active Ingredient" represents the "Carbazole" hereinbefore defined or a pharmaceutically acceptable salt solvate thereof. The stated dose represents that appropriate for the base; if a salt is used the dose should of course be increased appropriately.

EXAMPLE 10

Tablet

| Ingredient | Amount per tablet (mg) |
|---|---|
| Active Ingredient (compound of Ex. 5) | 60.0 |
| Lactose | 125.0 |
| Corn Starch | 50.0 |
| Polyvinylpyrrolidone | 3.0 |
| Stearic acid | 1.0 |
| Magnesium stearate | 1.0 |

EXAMPLE 11

Capsule

| Ingredient | Amount per capsule (mg) |
|---|---|
| Active Ingredient (compound of Ex. 6) | 60.0 |
| Lactose | 174.0 |
| Corn Starch | 174.0 |
| Stearic acid | 2.0 |

EXAMPLE 12

Ampoule

| Ingredient | Amount per ampoule |
|---|---|
| Active Ingredient (as a dihydrochloride salt of compound of Ex. 6) | 60.0 mg |
| Water for injection, q.s. | 1.0 ml |

EXAMPLE 13

Suppository

| Ingredient | Amount per suppository |
|---|---|
| Active Ingredient (compound of Ex. 1) | 60.0 mg |
| Theobroma oil (Cocoa Butter), q.s. | 2.0 g |

We claim:

1. The method of treating generalized anxiety disorder anxiety in a human which has been identified as exhibiting generalized anxiety disorder symptoms which comprises administering to said human an effective nontoxic generalized antianxiety disorder treatment amount of 9-[3-(3,5-cis-dimethylpiperazino)propyl]carbazole, a pharmaceutically acceptable salt thereof, or a pharmaceutically acceptable solvate of a pharmaceutically acceptable salt thereof.

2. The method of claim 1 in which the amount is 0.25 to 15 mg/kg of bodyweight calculated as base.

3. The method of claim 2 in which the amount is 1 to 10 mg/kg of bodyweight calculated as base.

4. The method of claim 1 or 2 in which said carbazole, salt or solvate are administered in a pharmaceutically acceptable carrier.

5. The method of treating a panic disorder in a human which has been identified as exhibiting panic disorder symptoms which comprises administering to said human an effective nontoxic antipanic disorder treatment of 9-[3-3,5-cis-dimethylpiperazino)propyl]carbazole, a pharmaceutically acceptable salt thereof, or a pharmaceutically acceptable solvate of a pharmaceutically acceptable salt thereof.

6. The method of claim 5 in which the amount is 0.25 to 15 mg/kg of bodyweight calculated as base.

7. The method of claim 6 in which the amount is 1 to 10 mg/kg of bodyweight calculated as base.

8. The method of claim 5 or 6 in which said carbazole, salt or solvate are administered in a pharmaceutically acceptable carrier.

9. The method of treating a phobic disorder in a human which has been identified as exhibiting phobic disorder symptoms which comprises administering to said human an effective nontoxic antiphobic disorder treatment amount of 9-[3-(3,5-dimethylpiperazino)-propyl]carbazole, a pharmaceutically acceptable salt thereof, or a pharmaceutically acceptable solvate of a pharmaceutically acceptable salt.

10. The method of claim 9 in which the amount is 0.25 to 15 mg/kg of bodyweight calculated as base.

11. The method of claim 10 in which the amount is 1 to 10 mg/kg of bodyweight calculated as base.

12. The method of claim 9 or 10 in which said carbazole, salt or solvate are administered in a pharmaceutically acceptable carrier.

13. The method of claim 9 or 10 in which the phobic disorder is Agoraphobia.

14. The method of treating post traumatic stress disorder in a human which has been identified as exhibiting post traumatic stress disorder symptoms which comprises administering to said human an effective nontoxic antipost traumatic stress disorder treatment amount of 9-[3-(3,5-cis-dimethylpiperazino)propyl]carbazole, a pharmaceutically acceptable salt thereof, or a pharmaceutically acceptable solvate of a pharmaceutically acceptable salt thereof.

15. The method of claim 4 in which the amount is 0.25 to 15 mg/kg of bodyweight calculated as base.

16. The method of claim 2 in which the amount is 1 to 10 mg/kg of bodyweight calculated as base.

17. The method of claim 14 or 15 in which said carbazole, salt or solvate are administered in a pharmaceutically acceptable carrier.

18. The method of treating obsessive compulsive disorder in a human which has been identified as exhibiting obsessional compulsive disorder symptoms which comprises administering to said human an effective nontoxic antiobsessive compulsive disorder treatment amount of 9-[3-(3,5-cis-dimethylpiperazino)propyl]carbazole, a pharmaceutically acceptable salt thereof, or a pharmaceutically acceptable solvate of a pharmaceutically acceptable salt thereof.

19. The method of claim 18 in which the amount is 0.25 to 15 mg/kg of bodyweight calculated as base.

20. The method of claim 19 in which the amount is 1 to 10 mg/kg of bodyweight calculated as base.

21. The method of claim 18 or 19 in which said carbazole, salt or solvate are administered in a pharmaceutically acceptable carrier.

22. The method of treating anxiety which is susceptable to treatment in a human which has been identified as exhibiting anxiety symptoms which comprises administering to said human an effective nontoxic antianxiety treatment amount of 9-[3-(3,5-cis-dimethylpiperazino)-propyl]carbazole a pharmaceutically acceptable salt thereof, or a pharmaceutically acceptable solvate of a pharmaceutically acceptable salt thereof.

23. The method of claim 22 in which the amount is 0.25 to 15 mg/kg of bodyweight calculated as base.

24. The method of claim 23 in which the amount is 1 to 10 mg/kg of bodyweight calculated as base.

25. The method of claim 22 or 23 in which said carbazole, salt or solvate are administered in a pharmaceutically acceptable carrier.

26. The method of claim 22 in which the carbazole or salt thereof is administered as part of a tablet or capsule.

* * * * *